United States Patent [19]
Javadi et al.

[11] Patent Number: 5,356,458
[45] Date of Patent: Oct. 18, 1994

[54] COMPUTERIZED CHEMICAL INJECTION SYSTEM FOR HYDROGEN SULFIDE CONTROL IN A WASTE WATER STREAM

[75] Inventors: Younes Javadi; Randy L. Jones, both of Sugerland; Douglas F. Werner, Kingwood, all of Tex.

[73] Assignee: Clearwater Industries Corporation, Metairie, La.

[21] Appl. No.: 74,271

[22] Filed: Jun. 8, 1993

Related U.S. Application Data

[63] Continuation of Ser. No. 743,815, Aug. 12, 1991, abandoned.

[51] Int. Cl.$^5$ .......................................... B01D 53/14
[52] U.S. Cl. ......................................... 95/13; 73/31.02; 73/864.34; 95/235; 210/916; 422/3; 422/5; 436/121
[58] Field of Search ............... 423/226, 228, 229, 563, 423/564; 436/39, 120, 121, 178; 422/3, 4, 83, 88, 90, 5; 210/739, 746, 85, 93, 94, 96.1, 143, 198.1, 750, 758, 759, 916, 634; 95/13, 235, 241; 73/31.02, 864.34

[56] References Cited

U.S. PATENT DOCUMENTS

| | | | |
|---|---|---|---|
| 2,496,354 | 2/1950 | Moyer et al. | 252/8.55 |
| 2,596,273 | 5/1952 | Moyer et al. | 252/8.55 |
| 2,596,425 | 5/1952 | Moyer et al. | 252/8.55 |
| 2,643,227 | 6/1953 | Hughes et al. | 252/8.55 |
| 2,643,977 | 6/1953 | Hughes et al. | 252/8.55 |
| 2,761,818 | 9/1956 | Draemel et al. | 423/229 |
| 2,860,030 | 11/1958 | Goldtrap et al. | 423/220 |
| 4,107,270 | 8/1978 | Ferrin et al. | 423/226 |
| 4,112,049 | 9/1978 | Bozzelli et al. | 423/226 |
| 4,380,586 | 4/1983 | Saltzman | 436/121 |
| 4,405,581 | 9/1983 | Savage et al. | 423/226 |
| 4,416,786 | 11/1983 | Knorre et al. | 210/916 |
| 4,436,713 | 3/1984 | Olson | 423/226 |
| 4,443,423 | 4/1984 | Olson | 423/226 |
| 4,515,759 | 5/1985 | Burnes et al. | 423/223 |
| 4,552,668 | 11/1985 | Brown et al. | 210/759 |
| 4,680,127 | 7/1987 | Edmondson | 423/226 |
| 4,748,011 | 5/1988 | Baize | 423/228 |
| 4,778,609 | 10/1988 | Koch et al. | 252/32.5 |
| 4,891,205 | 1/1990 | Bedell | 423/576.6 |
| 4,978,512 | 12/1990 | Dillon | 423/226 |
| 5,074,991 | 12/1991 | Weers | 210/749 |
| 5,104,527 | 4/1992 | Clinkenbeard | 210/198.1 |

FOREIGN PATENT DOCUMENTS

| | | | |
|---|---|---|---|
| 145014 | 8/1984 | Japan | 55/18 |
| 1134547 | 1/1985 | U.S.S.R. | 210/96.1 |

OTHER PUBLICATIONS

Publication "Elimination of Odor at Six Major Wastewater Treatment Plants", G. David Waltrip et al., Journal WPCF, vol. 57, No. 10, Oct. 1985.

*Primary Examiner*—Joseph W. Drodge
*Attorney, Agent, or Firm*—Pravel, Hewitt, Kimball & Krieger

[57] ABSTRACT

A system for continuously monitoring the hydrogen sulfide concentration present in the atmosphere above a waste water stream, such as a sewerage stream, and for controlling the amount and time of injecting a specified chemical into the waste water stream in order to control the quantity of hydrogen sulfide which would evaporate into the atmosphere. This system comprises the steps of obtaining a sample of atmosphere above the stream; routing the sample of air through a sensor for determining the concentration of hydrogen sulfide gas within the quantity of air determining the amount of an amine-based dopant to add to the waste water; sending a signal from the controller to a chemical injection pump for injecting the determined quantity of chemical compound into the waste water stream to absorb some of the hydrogen sulfide gas; continually monitoring the stream for determining the concentration of hydrogen sulfide gas in the stream following the introduction of chemical compound thereunto; and adding additional compound on a continuing basis, as needed, depending on the concentration of hydrogen sulfide within the stream.

4 Claims, 4 Drawing Sheets

COMPUTERIZED CHEMICAL INJECTION SYSTEM FOR HYDROGEN SULFIDE CONTROL IN A WASTE WATER STREAM

This is a continuation of co-pending application Ser. No. 07/743,815 filed on Aug. 12, 1991 now abandoned.

BACKGROUND OF THE INVENTION

1. Field Of The Invention

The system of the present invention relates to the monitoring and control of hydrogen sulfide gas in a waste water stream. More particularly, the present invention relates to a system for continuously monitoring the hydrogen sulfide concentration present in a waste water stream and controlling the quantity and time of automatically injecting a specified chemical into the waste water stream.

2. General Background

In the environmental waste water industry, it is critical that hydrogen sulfide gas, which is a toxic gas in certain concentrations, be monitored and controlled. For example, in a waste water stream such as a sewerage system of a municipality, depending upon the concentration of hydrogen sulfide in the waste water stream, some of it may evaporate into the air in its toxic gaseous form. It is therefore critical that the amount of gas in the atmosphere above the stream be closely monitored and controlled so that people do not come into contact with the deadly gas when working within the confines of the system.

In the present state of the art there are systems for monitoring the quantity of hydrogen sulfide gas in the air above a sewerage stream. However, these present state of the art methods require manual monitoring of the stream during specific time intervals and manual testing of the air through a standard testing procedure. This falls very far short of a system that continuously monitors the air above the waste water stream and controls the level of hydrogen sulfide through chemical injection.

There are several patents in the art which either address the system of monitoring hydrogen sulfide gas, or the chemical compounds which are added to the waste water stream in order to control the amount of hydrogen sulfide gas, the most pertinent patents being as follows:

| PATENT NO. | TITLE | ISSUE DATE |
|---|---|---|
| 4,978,512 | COMPOSITION AND METHOD FOR SWEETENING HYDROCARBONS | 12/18/90 |
| 4,891,205 | STABILIZED CHELATING AGENTS FOR REMOVING HYDROGEN SULFIDE | 01/02/90 |
| 4,778,609 | HYDROGEN SULFIDE SUPPRESSION WITH AMINE DERIVATIVE | 10/18/88 |
| 4,748,011 | METHOD AND APPARATUS FOR SWEETENING NATURAL GAS | 05/31/88 |
| 4,680,127 | METHOD OF SCAVENGING HYDROGEN SULFIDE | 07/14/87 |
| 4,515,759 | PROCESS OF REMOVING HYDROGEN SULFIDE FROM GAS MIXTURES | 05/07/85 |
| 4,443,423 | METHOD OF REMOVING HYDROGEN SULFIDE FROM GASES UTILIZING A POLYVALENT METAL CHELATE | 04/17/84 |
| 4,436,713 | METHOD OF REMOVING HYDROGEN SULFIDE FROM GASES UTILIZING A POLYVALENT METAL | 03/13/84 |
| 4,405,581 | PROCESS FOR THE SELECTIVE REMOVAL OF HYDROGEN SULFIDE FROM GASEOUS MIXTURES WITH SEVERELY STERICALLY HINDERED SECONDARY AMINO COMPOUNDS | 09/20/83 |
| 4,380,586 | METHOD AND APPARATUS FOR PHOTOMETRICALLLY MONITORING LOW LEVEL CONCENTRATION OF HYDROGEN SULFIDE IN ALKANOL AMINE | 04/19/83 |
| 4,112,049 | ABSORPTION OF SULFUR COMPOUNDS FROM GAS STREAMS | 09/5/78 |
| 4,107,270 | PROCESS FOR SIMULTANEOUS REMOVAL OF HYDROGEN SULFIDE AND WATER FROM A GAS MIXTURE WITHOUT | 08/15/78 |
| 2,860,030 | RECOVERY OF HYDROGEN SULFIDE AND/OR CARBON DIOXIDE SUBSTANTIALLY FREE FROM HYDROCARBONS AND | 11/11/58 |
| 2,761,818 | RECOVERY OF ETHANOLAMINES | 09/04/56 |

SUMMARY OF THE PRESENT INVENTION

The system of the present invention solves the shortcomings in the art. The invention provides a system for continuously monitoring the hydrogen sulfide concentration present in the atmosphere above a waste water stream, such as a sewerage system, and controlling the amount and time of injecting a specified chemical automatically into the waste water stream in order to control the quantity of hydrogen sulfide which would evaporate into the atmosphere. This system comprises the steps of identifying a particular waste water stream; obtaining a sample of the atmosphere immediately above the stream; routing the sample of air through a sensor for determining the precise concentration of hydrogen sulfide gas within the quantity of atmosphere; analyzing the concentration of hydrogen sulfide gas through the use of computer software in a controller; providing a quantity of chemical compound for introduction into the waste water stream; sending a signal from the controller into a chemical injection pump for injecting the specified quantity of chemical compound into the waste water stream to neutralize the hydrogen sulfide gas; continually monitoring the stream for determining the quantity of hydrogen sulfide gas in the stream following the introduction of chemical compound thereunto; and adding additional compound on a continuing basis, as needed, depending on the concentration of hydrogen sulfide within the stream.

Therefore, it is the principal object of the present invention to provide a comprehensive system of hydrogen sulfide control in a waste water stream through continuous monitoring of the stream and introduction of compound for neutralizing the hydrogen sulfide contained within the stream.

It is a further object of the present invention to provide a comprehensive hydrogen sulfide control system for a sewerage stream which would control the odor emission and would inhibit the corrosion of the pipe housing the waste water stream.

It is a further object of the present invention to provide a hydrogen sulfide control system which would increase the life of the waste water treatment facility structures through which the sewerage waste water stream travels.

It is a further object of the present invention to provide a complete hydrogen sulfide control system which would have no detrimental effects on the surrounding environment.

It is a further object of the present invention to provide a hydrogen sulfide control system which includes a typical compound treatment which is non-toxic and non-hazardous and would not produce formation of sludge to the system which would be costly to remove.

It is a further object of the present invention to provide a complete hydrogen sulfide control system which would enable workers within a waste water stream such as a sewerage plant to operate under safe conditions, and to monitor on a continuous basis the content of hydrogen sulfide within the waste water and the surrounding atmosphere.

BRIEF DESCRIPTION OF THE DRAWINGS

For a further understanding of the nature and objects of the present invention, reference should be had to the following detailed description taken in conjunction with the accompanying drawings, in which like parts are given like reference numerals, and wherein.

DETAILED DESCRIPTION OF THE PREFERRED EMBODIMENT

Figure 1:
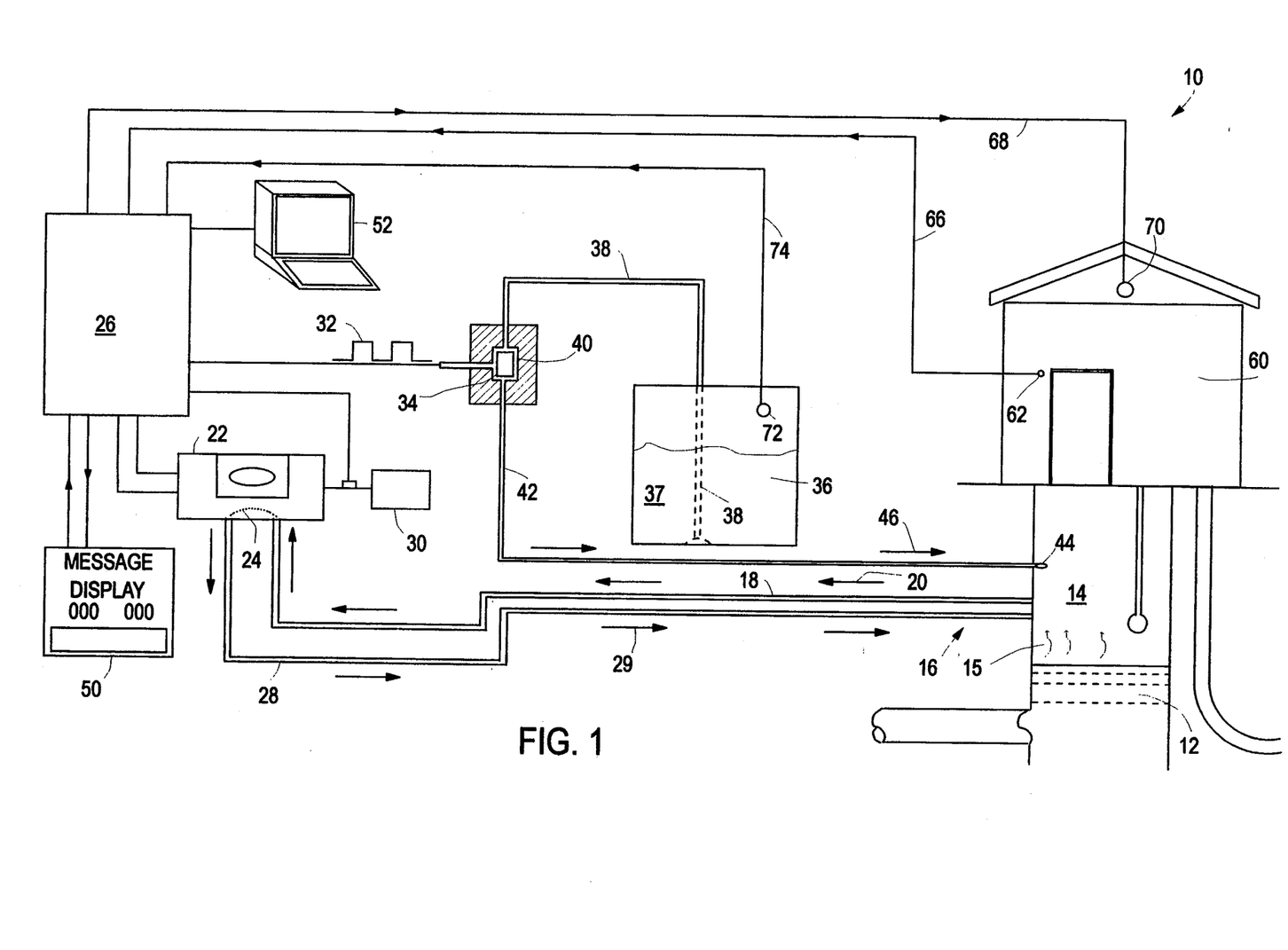
FIG. 1 illustrates an overall diagrammatical view of the preferred embodiment of the system of the present invention.
Figure 2:
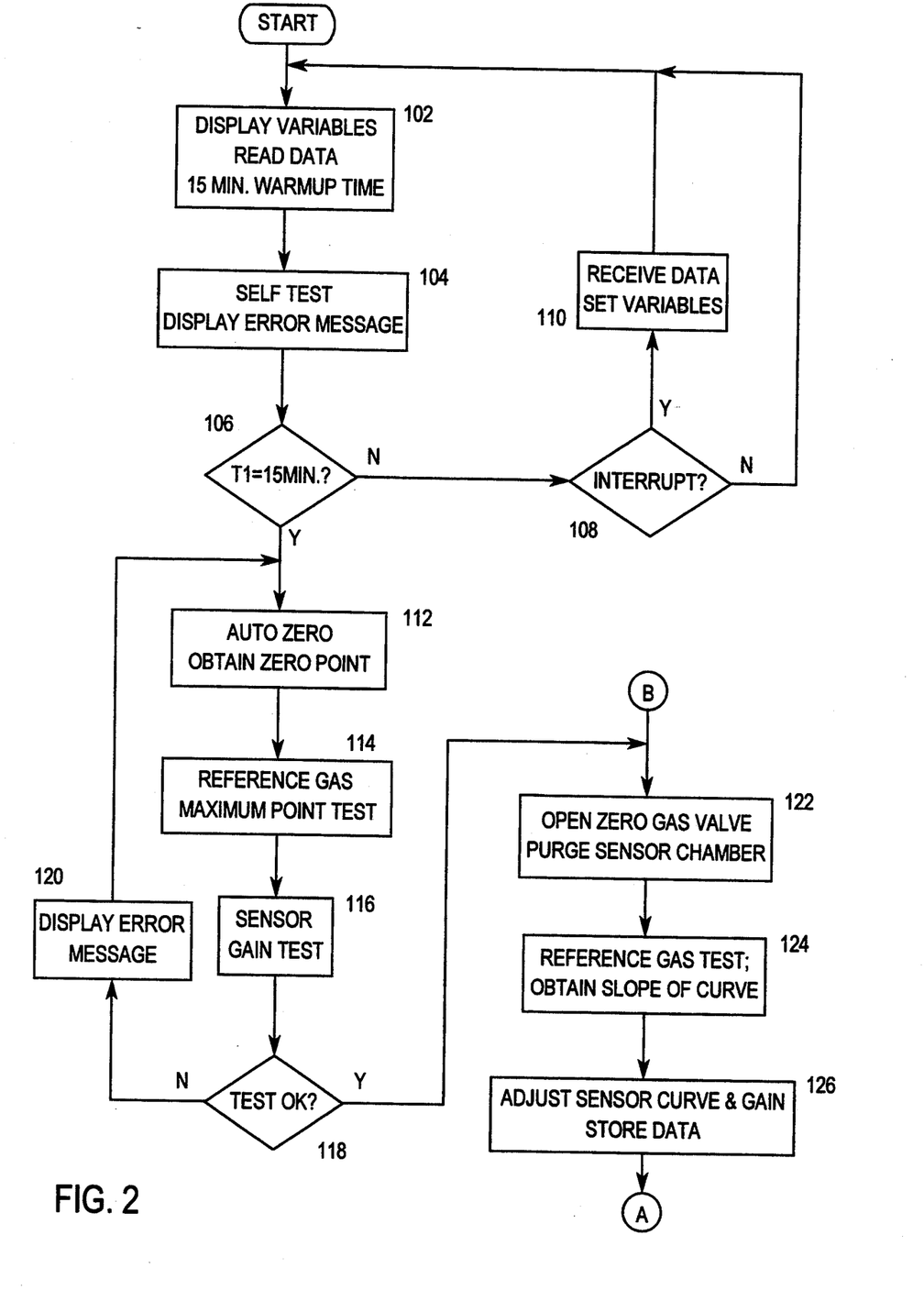
FIGS. 2 and 3 are flowchart diagrams illustrating operation of the controller of FIG. 1.
Figure 3:
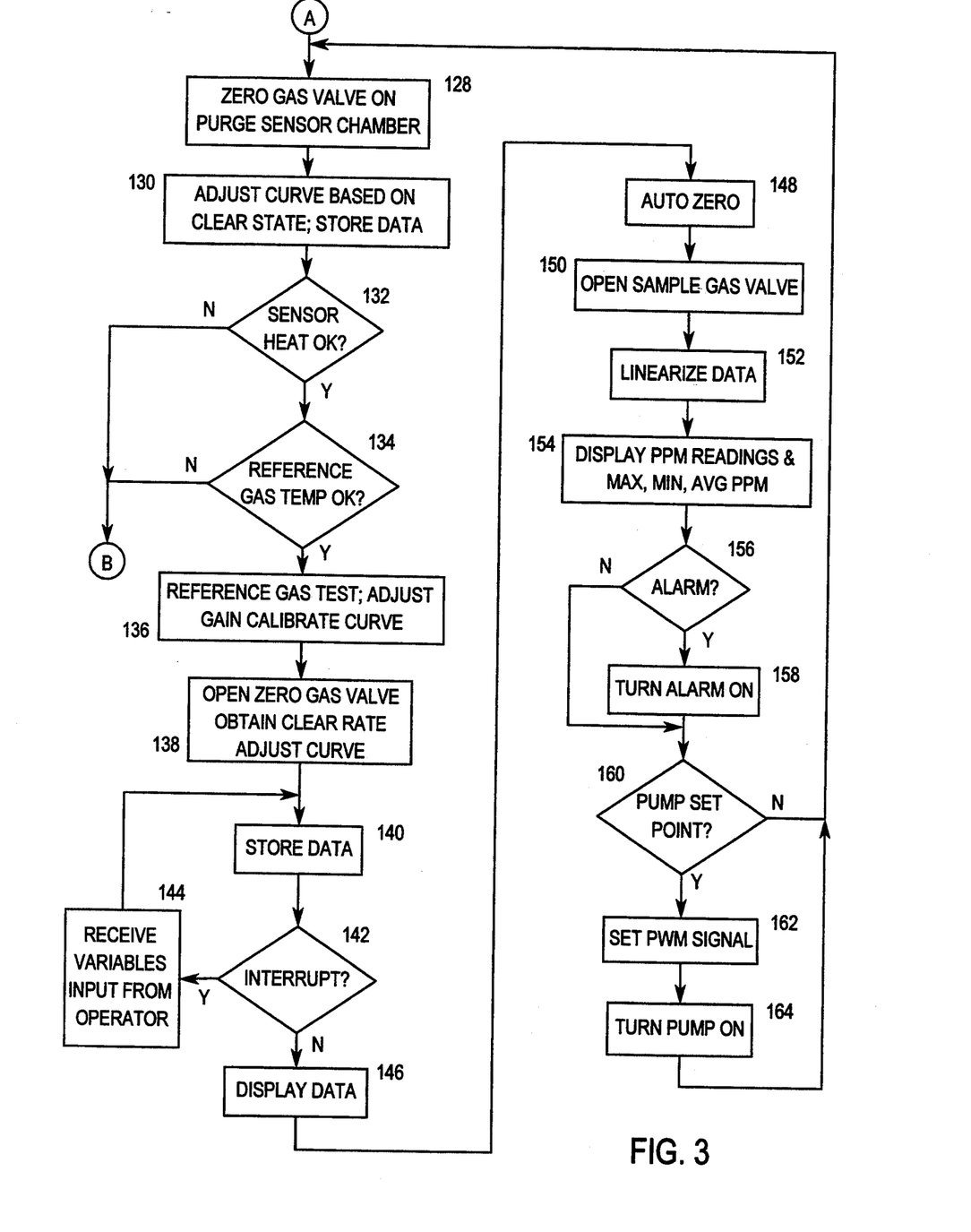

FIG. 1 illustrates the preferred embodiment of the system of the present invention by the numeral 10. As illustrated in FIG. 1, there is provided a waste water stream 12 which comprises a stream of fluid such as a sewerage stream from a municipality sewerage plant, but may also include any fluid stream which may have hydrogen sulfide ($H_2S$) gas entrained therein, said gas being released to the atmosphere 14 above the stream (Arrows 15). As illustrated, there is included a collection zone 16 through which a sample line 18 carries a specified quantity of the atmosphere 14 above the waste water stream 12 in the direction of arrows 20. The sample contained within line 18 is moved, through the use of a sample pump 22, and is introduced into a hydrogen sulfide gas sensor 24, which sensor 24 is contained within a hydrogen sulfide gas analyzer or control means 26, which is controlled by software. Alternatively, the sample line 18 may be located to draw directly from the waste water stream 12, with the entrained gas being released or removed prior to the sensor 24, with the gases then being analyzed by the sensor 24. A flowchart diagram illustrating the operation of the software is illustrated in FIGS. 2 and 3 and is discussed further below. The control means 26 preferably comprises a controller which includes a microcomputer, such as the 80196 microcontroller from Intel Corporation, analog inputs, pulse width modulated outputs, a modem, a terminal interface, various relay driver circuitry and an interface to a display.

The sensor 24 includes a sensor chamber (not shown) where gas samples may be evaluated. Following the specified sample of the gas being moved through the sensor 24, the gas is returned via the return line 28, in the direction of Arrows 29 to the atmosphere 14 above waste water stream 12. According to one embodiment of the invention, the sensor 24 is a typical sensor of the type manufactured by General Monitor located in California. In the preferred embodiment of the invention, the sensor 24 includes an ML-224-C $H_2S$ gas analyzer and a Model S-H100 hydrogen sulfide sensing element, both developed by Microline Controls, Inc. Microline Controls is located at 12999 Murphy Road, Suite B-7, Stafford, Tex. 77477. The controller means 26, for purposes of construction, contains the sensor 24. For purposes of the diagram, certain components are shown outside of the controller 26 for clarity. When the sensor 24 senses the presence of $H_2S$ gas within the sample, the sensor 24 provides a voltage signal to the controller 26, utilizing the software provided in the system, and the amount of hydrogen sulfide gas is quantified.

The sensor 24 preferably includes three valves (not shown) which are controlled by the controller 26 and are used for various operations. The sensor 24 includes a reference gas valve which connects to a tube containing a reference gas having a preset concentration of $H_2S$. This tube is used in determining the transfer characteristic curve or sensor curve (FIG. 4), which reflects the operation of the sensor 24. The sensor 24 also preferably includes an outside air valve which opens to the outside air, which is used to purge the sensor chamber of $H_2S$ and also to aid in determining the characteristics of the sensor curve. As is explained below, the operation of the sensor 24 varies during its lifetime, and thus the sensor curve is continually updated to properly reflect the current operation of the sensor 24. Finally, the sensor 24 includes a sample gas valve which connects the sample line 18 to the sensor chamber to allow samples of the atmosphere 14 to be evaluated.

Upon the quantification of the hydrogen sulfide gas within the sample, the analyzer or controller 26 provides a voltage signal 32 to the chemical injection means 34 as illustrated. The chemical injection means 34 includes a tank 36 housing a dopant chemical 37. Preferably, the dopant chemical comprises an amine-base-containing composition to be injected into the waste water stream.

The amine containing compound utilized as the dopant chemical in the present invention may be obtained by any suitable method that will yield the desired dopant amine. One particularly suitable method is by reacting an aldehyde with a compound containing at least one functional primary amine group.

The aldehyde compound useful in the present invention comprises at least one aldehyde group, and suitable aldehyde compounds include trimers of aldehydes such as, for example, paraformaldehyde and paraldehyde.

Generally the aldehyde will be of the formula:

$$\underset{RC=O}{\overset{H}{|}} \quad (X)$$

wherein group R is generally H or a substituted or unsubstituted hydrocarbon group. The group R is selected such that the water solubility of the final dopant amine product is maintained. Preferably R is selected from the group consisting of H and alkyl groups. Illustrative non-limiting alkyl groups include $C_1$ to $C_6$ alkyl groups. Most preferably R is selected from the group consisting of H, $$-CH_3, \quad -CH_2CH_3, \quad -CH_2CH_2CH_3 \text{ and } \underset{CH_3}{CH_3-CH-}.$$

The reactant amine utilized to make the dopant amine compound comprises at least one primary amine functional group. The reactant amine compound is generally a substituted or unsubstituted hydrocarbon with at least one primary amine functional group. The reactant amine compound is selected such that the water solubility of the final product is maintained. The reactant amine utilized in the present invention may even comprise mixtures of the various reactant amines.

Preferably, the reactant amine utilized in the present invention is selected from the group consisting of polyalkylene amines, alkanolamines and mixtures thereof.

The preferable polyalkylene amines suitable for use in the present invention are of the general formula:

$$NH_2(CH_2CH_2NH)_nCH_2CH_2NH_2 \quad (XI)$$

wherein n is an integer in the range of about 0 to about 3.

Exemplary non-limiting examples of polyalkylene amines suitable for use in the present invention include those of the formula:

$$NH_2CH_2CH_2NH_2;$$

$$NH_2CH_2CH_2NHCH_2CH_2NH_2; \text{ and}$$

$$NH_2CH_2CH_2NHCH_2CH_2NHCH_2CH_2NH_2.$$

Once the polyalkylene amines of general formula XI are reacted with the aldehydes of general formula X, the resulting dopant amine is obtained:

$$\underset{RC=N(CH_2CH_2NH)_n-CH_2CH_2N=CR}{\overset{H \qquad\qquad\qquad\qquad H}{|\qquad\qquad\qquad\qquad\quad|}} \quad (XIIIA)$$

wherein R is as defined above.

When injected into the waste water stream to react with the $H_2S$, the dopant amine of general formula XIIIA will form the following by-product:

$$\underset{\underset{SH}{|}}{\overset{H}{|}}\text{RC}-N(CH_2CH_2NH)_n-CH_2CH_2N-\underset{\underset{SH}{|}}{\overset{H}{|}}\text{CR} \quad (XIVA)$$

wherein one or both of the —SH groups has attached itself to the dopant amine.

Alkanolamines that are preferred as the reactant amines of the present invention are of the general formula:

$$H_2N-R'-OH \quad (XII)$$

wherein R' is a $C_1$ to $C_4$ hydrocarbon group, preferably a $C_1$ to $C_4$ alkyl group.

Exemplary non-limiting examples of alkanolamines that may be utilized in the present invention include those of the formula;

$$H_2N(CH_2)_3OH \quad \text{(monoethanolamine)};$$

$$\underset{CH_3}{H_2NCH_2CHOH} \quad \text{(isopropanolamine)};$$

$$H_2N(CH_2)_3OH; \text{ and}$$
$$H_2N(CH_2)_4OH.$$

Of these illustrative examples of the most preferred alkanolamines are monoethanol amine and isopropanol amine.

The alkanolamines of general formula XII will react with the aldehyde of general formula X to form the following dopant amines:

$$\underset{RC=N-R'\,OH}{\overset{H}{|}} \quad (XIIIB)$$

wherein R and R' are as defined above.

When injected into the waste water stream to react with the $H_2S$, the dopant amine of general formula XIIIB will form the following by-product:

$$\underset{\underset{SH}{|}}{\overset{H}{|}}\text{RC}-N-R'\,OH \quad (XIVB)$$

wherein R and R' are as defined above.

Illustrative examples of typical reactions are as follows:

A. Enimine formation from alkanolamines

1) $\underset{O}{\overset{CH_2}{\|}} + NH_2CH_2CH_2OH \longrightarrow$ $$HOCH_2-NHCH_2CH_2OH \quad (I)$$

2) $HOCH_2-NHCH_2CH_2OH-H_2O \longrightarrow$ $$CH_2=N-CH_2CH_2OH \quad (II)$$

3) $CH_2=N-CH_2CH_2OH + HSH \longrightarrow$ $$\underset{\underset{SH}{|}}{CH_3-N-CH_2CH_2OH} \quad (III)$$

B. Enimine formation from polyalkylene amines:

4) $\underset{O}{\overset{CH_2}{\|}} + NH_2CH_2CH_2NH_2 \longrightarrow$ $$HOCH_2NHCH_2CH_2NHCH_2OH \quad (IV)$$

5) $HOCH_2NHCH_2CH_2NHCH_2OH-H_2O \longrightarrow$ $$CH_2=N-CH_2CH_2N=CH_2 \quad (V)$$

6) $CH_2=N-CH_2CH_2N=CH_2 + HSH \longrightarrow$ $$\underset{\underset{SH}{|}}{CH_2-N}-CH_2CH_2N=CH_2 \quad (VI)$$

7) $\underset{\underset{SH}{|}}{CH_2-N}-CH_2CH_2N=CH_2 + HSH \longrightarrow$ $$\underset{\underset{SH}{|}}{CH_2-N}-CH_2CH_2\underset{\underset{SH}{|}}{N}-CH_2 \quad (VII)$$

The dopant amine compound is contained within tank 36, with tank 36 having a line 38 extending downward at 39 into the compound contained within tank 36. Line 38 is connected on its second end to a chemical injection pump 40, which has an injection line 42 leading into the sample zone 16 at an injection nozzle 44.

In the system, upon the chemical injection pump 40 receiving a pulse width modulated (PWM) signal 32 from controller or analyzer 26, the chemical injection pump 40 removes a quantity of dopant amine compound from container 36 based on the width of the signal pulse and injects the compound through line 42 into the waste water stream at nozzle 44 in the direction of arrows 46. This injection of compound absorbs a certain quantity of the $H_2S$ gas in order to reduce the amount of $H_2S$ gas flowing or moving into the atmosphere from the waste water stream. This system enables the constant receiving of a sample of gas from the atmosphere above the waste water stream, sensing the presence of $H_2S$ gas, quantifying the amount of $H_2S$ gas in a sample, and signalling the pump to inject a quantity of chemical into the stream to reduce the presence of gas above the stream. The entire system is continuous and is controlled by the software contained in the controller or analyzer 26, which is described below.

As further illustrated in FIG. 1, there is included a message display board 50, which displays the necessary information that an operator of this system needs in order to continue to operate and to monitor the operation of the system as it controls the quantity of $H_2S$ gas. Further, there is a computer 52 having a viewing monitor. An operator may use the computer 52 to view the information on the computer screen and to feed data into the controller 26, as the need arises. These means of monitoring the data are controlled by the controller 26.

As further illustrated in FIG. 1, there is a control room 60 positioned directly above the waste water stream 12, which is utilized in the operation of monitoring of the stream. In order to provide safety to workers or other persons entering the control room 60, there is further provided a second $H_2S$ gas sensor 62 contained within the control room 60. The data from sensor 62 is provided to the controller 26 via signal 66. In the preferred embodiment, the controller 26 provides a second signal 68 to the control room 60 when the pressure of $H_2S$ gas within the control room 60 reaches a critical level to activate a warning light 70 to warn anyone entering the room that the level of hydrogen sulfide gas within the room may be at a dangerous level.

For purposes of monitoring the level of dopant compound within tank 36, there is a level indicator means 72 contained within tank 36 which constantly provides a signal 74 to the controller 26 so as to maintain a constant monitoring of the amount of compound contained within tank 36. Appropriate alarms are provided if the level goes below a preset point.

The controller sample pump 22, which is used to pump the sample atmosphere 14 to the sensor 24, is desirably installed near a lift station/manhole to deliver a preset volume of air sample to the sensor manifold. The hydrogen sulfide control concentration is then calculated. Based upon the hydrogen sulfide concentration, a command is sent out to the chemical injection pump 40 to commence pumping certain volumes of chemical to reduce the hydrogen sulfide present. The chemical injection pump 40 is desirably packaged in a NEMA7 weatherproof enclosure and installed in a protected environment. The chemical injection pump 40 may be located at the same location as the sensor 24 or may alternatively be located to provide dopant chemicals to a location upstream of the location being monitored by the sensor 24. In the remote location case, appropriate communication circuitry is utilized.

Referring now to FIGS. 2 and 3, a flowchart diagram illustrating the operation of the software in the controller 26 is shown. The flowchart is shown in two portions for clarity, and interconnections between the two Figures are referenced by the circled letters A and B. The flowchart is for operation with a single sensor only, with conversion to a dual sensor readily apparent to one skilled in the art. On power up or reset, the controller 26 begins in step 102 and displays a number of variables and reads any input data provided by an operator. The operator will provide information relating to the dopant amine chemical, such as concentrations and pump rates, to the various alarm levels and other preset conditions. In step 104, the controller 26 performs a self test and, if an error occurs, displays an error message. In step 106, the controller 26 determines if 15 minutes have elapsed since the controller 26 was turned on. The sensor 24 generally requires a 15 minute warmup time before it may begin operation. If 15 minutes have elapsed, the controller 26 advances to step 112. If 15 minutes have not yet elapsed, the controller 26 advances to step 108. In step 108, the controller 26 determines if an interrupt has been generated, reflecting whether an operator has input or changed certain variables with regard to the operation of the system. It is noted that the interrupt will generally be asynchronous. However, the interrupt is represented as a step in the flowchart for clarity. If an interrupt has been generated, the controller 26 advances to step 110 where it receives the data input from the user and sets the variables accordingly. If an interrupt has not been generated, the controller 26 returns to step 102 and repeats the sequence of steps 102–110 until the 15 minute warmup time has completed.

Figure 4:
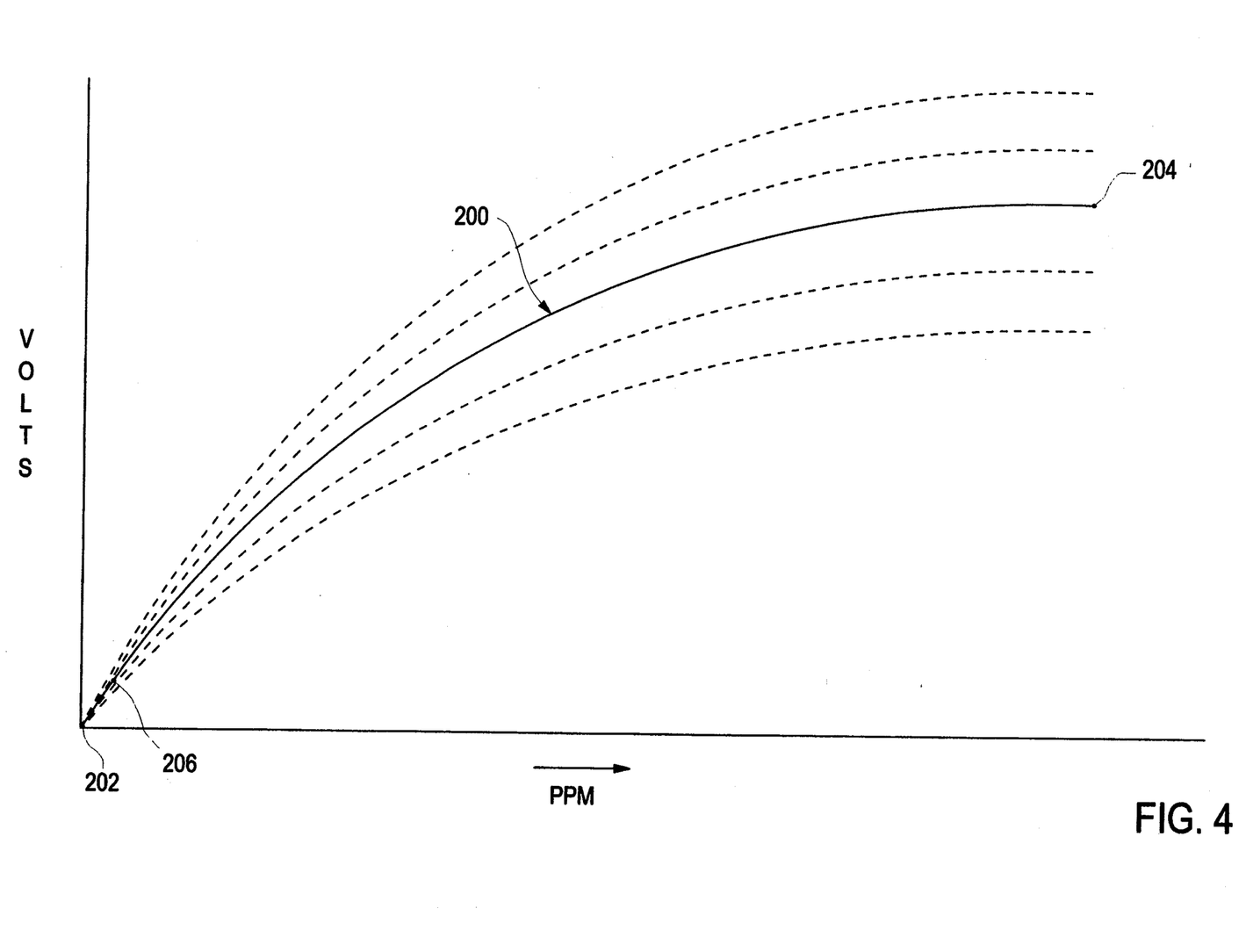
FIG. 4 is a graph illustrating a family of curves demonstrating the operation of the sensor of FIG. 1.

In step 112, the controller 26 opens the outside valve to the outside air and transfers the outside air into the sensor chamber to perform an auto zero function. Referring now to FIG. 4, a graph illustrating a family of curves which represent the transfer characteristic of the sensor 24, referred to as the sensor curve, is shown. The graph plots the voltage output from the sensor 24 versus the parts per million (ppm) concentration of $H_2S$ in the gas being evaluated. During the lifetime of the sensor 24, the sensor curve will change due to a buildup of impurities in the sensor 24. Therefore, at any point during the lifetime of the sensor 24, any of a family of curves shown in FIG. 3 may represent the characteristic of the sensor at that time.

In step 112, the outside valve is opened to allow outside air into the sensor chamber. This outside air contains no $H_2S$ and is used to find the voltage output of the sensor 24 when a gas containing zero $H_2S$ is applied to the sensor 24. This allows the controller 26 to determine the zero point 202 of the transfer characteristic or sensor curve 200 of the sensor 24. In step 114, the controller 26 opens the reference gas valve to the tube containing the reference gas having a preset concentration of $H_2S$, preferably approximately equal to the desired maximum sensitivity range. This valve is preferably opened for approximately 45 seconds to build up the concentration of $H_2S$ in the sensor chamber to saturate the sensor 24 with the maximum amount of $H_2S$ that the sensor 24 can absorb. The controller 26 reads the voltage output from the sensor 24 at this time to read the maximum voltage output or the high point 204 of the sensor curve 200. The controller 26 uses the information generated from this test to aid in formulating the sensor curve 200 in FIG. 3.

In step 116, the voltage output from the sensor 24, which passes through an amplifier stage in the controller 26, is measured by the controller 26 to ensure that the amplifier includes sufficient gain to enable the controller 26 to read the voltage provided from the sensor 24. The voltage output from the sensor 24 is in the millivolt range, and thus the amplifier is needed to ensure that a readable voltage is provided to the controller 26. Preferably, the amplifier has a lower gain during the early life of the sensor 24. The controller 26 determines the amount of gain provided by the amplifier and stores this data in memory. It is noted that, as the sensor 24 ages, the gain of the amplifier will be increased by the controller 26, so that the controller 26 receives a voltage output which is consistent with the ppm of $H_2S$ that is read by the sensor 24 and so that maximum accuracy from the analog/digital converter contained on the controller 26 can be maintained.

In step 118, the controller 26 determines if the test results were properly received. If not, an error message is displayed in step 120, and the controller 26 repeats steps 112–116. If the test results were properly received and stored, the controller 26 advances to step 122. In step 122, the sensor chamber is purged of $H_2S$ by opening the outside valve so that a subsequent test can be performed. Here it is noted that it is not critical that the sensor 24 return to the exact zero point where it was after the previous auto zero operation, as is explained below.

In step 124, the reference gas valve is opened for a small amount time, preferably between 1 millisecond and 1 second, and the reference gas containing a fixed ppm of $H_2S$ is supplied to the sensor chamber during this brief period of time. The voltage output is read by the controller 26 during this time, and the controller 26 uses the rate of change of the voltage produced by the sensor 24 in response to this reference gas to determine the slope of the curve 200. It is noted that the length of time that the reference gas valve remains open depends upon the age of the sensor, i.e., the controller 26 will maintain the reference gas valve open for a longer period for an older sensor because an older sensor generally requires a longer amount of time to respond to the reference gas. The controller 26 maintains the reference gas valve open until a desired change occurs in the voltage produced by the sensor 24, i.e., the voltage reaches a desired point 206. The controller 26 uses this change to determine the slope of the reference curve. Also, it is generally not important whether the sensor 24 is operating at the zero point of the sensor curve 200 during this test since the reference gas valve is generally open for less than 1 second and the slope of the curve is what is being determined. Utilizing this information, the controller 26 adjusts the sensor curve 200 in step 126 to closely match the operation of the sensor 24 for this particular measuring sequence. The controller 26 also uses this data to adjust the gain of the amplifier. Also, in step 126 the controller 26 stores respective data such as the minimum and maximum reading of the sensor curve, the average reading, etc., in EEPROM (electronically erasable programmable read only memory) and in RAM.

The controller 26 advances from step 126 to step 128 (FIG. 3), wherein the controller 26 opens the outside valve to the outside air to purge the sensor chamber. The controller 26 monitors the sensor voltage output as the sensor chamber is purged in step 128 to determine the rate at which the chamber is purged, referred to as the clear rate. This data is used to ensure that the slope of the sensor curve is consistent with the prior reading performed in step 124. In step 130, the controller 26 makes minor adjustments to the sensor curve based on the clear rate determined in step 128. Also in step 130, the controller stores the generated data in memory.

In step 132, the controller 26 determines the temperature of the sensor 24 to ensure that the sensor 24 is operating at the proper temperature, which is approximately 180° F.±5°. Here it is important that the sensor temperature remain in the prescribed range to ensure the integrity of the voltage readings supplied by the sensor 24. If the sensor temperature is not within the prescribed range, the controller 26 returns to step 124 and repeats the operations performed therein. If the sensor temperature is determined to be within the prescribed range, the controller 26 advances from step 132 to step 134. In step 134, the controller 26 determines if the reference gas temperature is adequate, i.e., is it approximately equivalent to the ambient temperature in the relevant atmosphere 14 being tested. If not, the controller 26 returns to step 124 and repeats the operations performed therein. If the reference gas temperature adequately corresponds to the atmosphere temperature, the controller advances to step 136.

In step 136, the controller 26 opens the reference gas valve to expose the sensor to the reference gas for the time period that the valve was opened in step 124. At this time, the controller 26 monitors several variables, including time, voltage, ppm of $H_2S$, and the gain of the amplifier and determines if the sensor is operating consistently with the manner in which the sensor operated in step 124 when this same test was performed. In effect, the controller 26 determines whether the sensor is operating according to the sensor curve 200 which was generated in the previous steps. The controller 26 uses this information to recalibrate or do a final fine tuning of the sensor curve 200 to ensure that the curve 200 more closely approximates the actual operation of the sensor 24. The controller 26 also uses this information to adjust the gain of the amplifier.

The controller 26 advances from step 136 to step 138 where the outside valve is opened to enable the controller 26 to determine the clear rate of the sensor chamber. The controller 26 uses this data to again adjust the sensor curve accordingly. In step 140, the controller 26 stores the relevant data generated by the tests in steps 136 and 138. In step 142, the controller 26 determines if an interrupt has been generated. If so, the controller 26 receives data input from an operator in step 144 and then returns to step 140. If no interrupt has been generated in step 142, the controller 26 displays recorded variables to the operator in step 146 such as the maximum and minimum clear rate, as well as other data relevant to the sensor curve 200.

In step 148, the controller 126 performs the auto zero function to again determine the zero point 202 of the sensor curve 200. This operation also purges the sensor chamber in the sensor 24. The controller 26 then advances from step 148 to step 150 and opens the sample gas valve to the sample line 18, which carries a sample of the atmosphere 14 above the stream 12. The sample of atmosphere 14 enters the sensor chamber, where the sensor 24 evaluates the concentration of $H_2S$ and provides a corresponding voltage to the controller 26. The controller 26 receives the voltage and performs a track and hold operation. The controller 26 then linearizes the received voltage. In this linearization step, the received voltage is referenced to the final sensor curve to develop the corresponding ppm of $H_2S$ value.

In step 154, the controller 26 generates a signal to the computer 52 and display board 50 to display the ppm reading and the maximum, minimum, and average $H_2S$ concentration levels. The controller 26 then advances from step 154 to step 156 where the controller 26 checks the $H_2S$ ppm reading to determine if the alarm 70 should be enabled. If so, the controller 26 generates the signal on line 68 to the alarm 70 in step 158, and the alarm light 70 is turned on. The controller 26 then advances to step 160. If the ppm reading is such that the alarm 70 need not be turned on in step 156, the controller 26 advances to step 160, where it determines if the chemical injunction pump 40 should be enabled to provide the chemical compound from the container 36 through line 42 into the waste water stream 12. If the $H_2S$ ppm concentration is such that the pump 40 should be enabled, the controller 26 advances to step 162 where a pulse width modulated signal is generated to enable the pump 40 in step 164. The width of the pulse in the PWM signal determines the length of time that the chemical injunction pump 40 provides the chemical compound to the waste water stream 12. The signal parameters are based on the particular dopant chemical and concentrations in use at the particular location, this information having been previously provided by the operator. The controller 26 then returns from step 164 to step 128. If the ppm reading is such that the chemical injunction pump 40 need not be enabled in step 160, the controller 26 returns from step 160 to step 128.

Upon return to step 128, the controller 26 repeats steps 128-164, preferably every 2 to 3 minutes, to continue to update the sensor curve and the amplifier gain and evaluate samples from the atmosphere 14 above the waste water stream. Thus, the sensor curve 200 is continuously calibrated so that the curve closely approximates the current operation of the sensor. In addition, the gain of the amplifier is continuously adjusted to reflect the decreasing response of the sensor as the sensor 24 ages. In this manner, the controller 26 is able to more closely determine the correct ppm reading from the voltage output of the sensor throughout the lifetime of the sensor 24. This continuous loop allows constant and accurate monitoring of the $H_2S$ concentration to assist in maintaining levels below hazardous or dangerous points.

It is foreseen that this control system for monitoring and controlling the presence of hydrogen sulfide gas within the atmosphere above a liquid stream, could also be modified to monitor the quantity of hydrogen sulfide gas within the liquid itself, as opposed to the atmosphere above the liquid. It is foreseen that this system, with slight modifications, could be utilized in the same manner, and would therefore enable the monitoring of the system through the fluid itself, rather than after the $H_2S$ gas has moved into the atmosphere above the stream.

Because many varying and different embodiments may be made within the scope of the inventive concept herein taught, and because many modifications may be made in the embodiments herein detailed in accordance with the descriptive requirement of the law, it is to be understood that the details herein are to be interpreted as illustrative and not in a limiting sense.

We claim:

1. A computerized chemical injection system for controlling hydrogen sulfide emissions from a waste water stream, comprising:
   a) removing a quantity of atmosphere from above a portion of the waste water stream;
   b) sensing whether the quantity of atmosphere removed includes hydrogen sulfide gas therein;
   c) analyzing the concentration of hydrogen sulfide gas within the removed air, through the use of an analyzer;
   d) providing a specified quantity of dopant amine chemical compound into the waste water stream, the quantity depending on the level of hydrogen sulfide derived from the analyzer, to absorb the $H_2S$ gas; and
   e) continuously repeating steps a–d, to reduce concentrations of hydrogen sulfide sensed within the atmosphere above the stream,
   wherein said quantity of atmosphere above the waste water stream is removed from above the stream through a pump device.

2. A computerized chemical injection system for controlling hydrogen sulfide emissions from a waste water stream comprising:
   a) removing a quantity of atmosphere from above a portion of the waste water stream;
   b) sensing whether the quantity of atmosphere removed includes hydrogen sulfide gas therein;
   c) analyzing the concentration of hydrogen sulfide gas within the removed air, through the use of an analyzer;
   d) providing a specified quantity of dopant amine chemical compound into the waste water stream, the quantity depending on the level of hydrogen sulfide derived from the analyzer, to absorb the $H_2S$ gas; and
   e) continuously repeating steps a–d, to reduce concentrations of hydrogen sulfide sensed within the atmosphere above the stream,
   wherein the dopant amine chemical compound provided into the stream has a general formula selected from the group consisting of wherein R' is a $C_1$ to $C_4$ alkyl group, and and wherein R is selected from the group consisting of H and $C_1$ to $C_6$ alkyls.

3. A computerized chemical injection system for controlling hydrogen sulfide emissions from a waste water stream, comprising:

a) removing a quantity of atmosphere from above a portion of the waste water stream;

b) sensing whether the quantity of atmosphere removed includes hydrogen sulfide gas therein;

c) analyzing the concentration of hydrogen sulfide gas within the removed air, through the use of an analyzer;

d) providing a specified quantity of dopant amine chemical compound into the waste water stream, the quantity depending on the level of hydrogen sulfide derived from the analyzer, to absorb the $H_2S$ gas;

e) continuously repeating steps a–d, to reduce concentrations of hydrogen sulfide sensed within the atmosphere above the stream; and f) monitoring the level of hydrogen sulfide gas within the atmosphere of a control room above the waste water stream.

4. A computerized chemical injection system for controlling hydrogen sulfide concentration in a sewerage stream, comprising:

a) removing a quantity of atmosphere from above a portion of the sewerage stream;

b) sensing the presence of hydrogen sulfide gas within the quantity of atmosphere removed;

c) analyzing the concentration of hydrogen sulfide gas within the removed atmosphere;

d) pumping a specified quantity of a dopant amine chemical compound into the sewerage stream, said quantity depending on the concentration of hydrogen sulfide gas sensed in the stream, to absorb at least part of the hydrogen sulfide gas present;

e) repeating steps a) through d) on a continuous basis through the use of a computerized analyzer; and f) monitoring the level of hydrogen sulfide gas contained within the atmosphere of a control room above the waste water stream and providing an alarm upon the presence of predetermined levels of hydrogen sulfide gas in the room.

* * * * *